United States Patent [19]

Matsumoto et al.

[11] Patent Number: 4,925,980
[45] Date of Patent: May 15, 1990

[54] PROCESS FOR PRODUCING METHACRYLIC ACID AND A CATALYST

[75] Inventors: Mutsumi Matsumoto; Yoshimasa Seo, both of Takasaki, Japan

[73] Assignee: Nippon Kayaku Kabushiki Kaisha, Tokyo, Japan

[21] Appl. No.: 697,685

[22] Filed: Feb. 1, 1985

Related U.S. Application Data

[63] Continuation of Ser. No. 363,008, Mar. 29, 1982, abandoned, which is a continuation of Ser. No. 44,269, May 31, 1979, abandoned.

[30] Foreign Application Priority Data

Jun. 21, 1978 [JP] Japan .................................. 53-74274

[51] Int. Cl.$^5$ ...................... C07C 51/25; C07C 57/055
[52] U.S. Cl. ..................... 562/534; 502/209; 562/535
[58] Field of Search ................. 562/534, 535; 502/209

[56] References Cited

U.S. PATENT DOCUMENTS

| | | | |
|---|---|---|---|
| 3,875,220 | 4/1975 | White et al. | 562/535 |
| 4,017,423 | 4/1977 | White et al. | 562/535 |
| 4,042,625 | 8/1977 | Matsuzawa et al. | 562/535 |
| 4,113,770 | 9/1978 | Akiyama et al. | 562/535 |
| 4,320,227 | 3/1982 | Matsumoto et al. | 562/535 X |
| 4,745,217 | 5/1988 | Matsumoto et al. | 562/535 X |

FOREIGN PATENT DOCUMENTS

| | | |
|---|---|---|
| 2514232 | 10/1975 | Fed. Rep. of Germany ...... 562/535 |
| 2608583 | 9/1976 | Fed. Rep. of Germany ...... 562/535 |
| 2722375 | 12/1977 | Fed. Rep. of Germany . |
| 2304597 | 10/1976 | France . |
| 2306188 | 10/1976 | France . |
| 52-62220 | 5/1977 | Japan . |
| 52-68122 | 6/1977 | Japan . |
| 1487765 | 10/1977 | United Kingdom . |
| 1492185 | 11/1977 | United Kingdom . |
| 1523849 | 9/1978 | United Kingdom . |

Primary Examiner—Vivian Garner
Attorney, Agent, or Firm—Wegner & Bretschneider

[57] ABSTRACT

The present invention relates to a process for producing methacrylic acid by oxidizing methacrolein in vapor phase with molecular oxygen or a gas containing molecular oxygen, characterized in that the oxidation is carried out in the presence of a catalyst having a composition shown by the following formula:

$$Mo_a V_b P_c X_d Y_e O_f$$

wherein Mo, V, P and O respectively represent molybdenum, vanadium, phosphorus and oxygen; X represents at least one element selected from the group consisting of potassium, rubidium, cesium, and thallium; Y represents at least one element selected from the group consisting of copper, silver, tin, thorium, germanium, nickel, iron, cobalt, titanium, rhenium, chromium, cerium, antimony and magnesium; and a, b, c, d, e and f denote the atomic ratio of respective elements where, a is 10, b is a number of 6 or less than 6 excluding 0, preferably 0.5 to 3, c is a number of 0.5 to 6, preferably 0.5 to 3, d is a number of 0.5 or less than 0.5 excluding 0, preferably 0.01 to 0.3, e is a number of 5 or less than 5 excluding 0, preferably 0.01 to 1 and f is a number determined by the valence and atomic ratio of the other elements and usually is a number of 35 to 80, and comprising heteropolyacid having the elements above-mentioned as its components and X-metal salt of the heteropolyacid both of which are present in a mixed state, and relates also to the above-mentioned catalyst.

5 Claims, No Drawings

PROCESS FOR PRODUCING METHACRYLIC ACID AND A CATALYST

This application is a continuation of U.S. application Ser. No. 363,008, filed Mar. 29, 1982, now abandoned which is a continuation of U.S. application Ser. No. 044,269 filed May 31, 1979, now abandoned.

DETAILED DESCRIPTION OF THE INVENTION

The present invention relates to a process for producing methacrylic acid by catalytic oxidation of methacrolein in vapor phase, characterized by the use of a novel catalyst with long life, high activity and high selectivity, and relates also to the above-mentioned novel catalyst.

Recently, a number of catalysts have come to be proposed for catalyzing the oxidation of methacrolein in vapor phase, however, they have not been industrially put to operation as in the process for producing acrylic acid by oxidation of acrolein. The reason is considered to be due to the fact that the yield of the object (methacrylic acid) obtained by the use of such catalysts is not so high as in the case of the production of acrylic acid and that the catalysts have short life insufficient to exhibit constant activity for a long term.

The majority of the catalysts proposed for catalytic oxidation of methacrolein in vapor phase are those having molybdenum-phosphorus as the major component, and structurally they are considered to be phosphomolybdates, for instance, mainly ammonium or alkali salts of heteropolyacid thereof.

However, the largest disadvantage of these catalysts is their short life as a catalyst, and in the long run of reaction the decomposition of the structure of heteropolyacid salt slowly occurs accompanying the reduction of its catalytic activity. Accordingly, such catalysts do not have sufficiently long life for industrial use, and in order to maintain the catalytic activity for a long time in such a catalytic system it is inevitable under the existing circumstances to choose the extremely mild reaction conditions far remote from those requested by economy.

One of the inventors of the present invention has made trials of improving the low activity and low selectivity as well as the above-mentioned short life of the conventional catalyst for catalytic oxidation of methacrolein in vapor phase and has found that a composition having Mo-V-P-O as the main body, added with various elements to become a structure of heteropolyacid or a reduced-type composition thereof is high in activity and selectivity and, in particular, is a stable catalyst in view of its catalytic life period. His discovery of this phenomenon lead him to submit German Patent Application P 27 39 779.1-41 (published as DOS 27 39 779) and U.S. patent application Ser. No. 948,761, filed Oct. 5, 1978, now abandoned.

The inventors of the present invention studied further the catalyst system above-mentioned and have found that the heteropolyacid catalyst having phosphovanadomolybdic acid as its main constituent added with various elements shows a markedly improved activity and selectivity without losing its characteristic long catalytic life provided it coexisted with a potassium, rubidium, cesium or thallium salt of the heteropolyacid, and they have completed the present invention.

Namely, the present invention relates to a process for producing methacrylic acid by oxidizing methacrolein in vapor phase with molecular oxygen or a gas containing molecular oxygen characterized in that the oxidation above-mentioned is carried out in the presence of a catalyst which has a composition of the following formula:

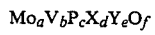

$Mo_aV_bP_cX_dY_eO_f$ wherein Mo, V, P and O respectively represent molybdenum, vanadium, phosphorus and oxygen; X represents at least one element selected from the group consisting of potassium, rubidium, cesium and thallium; Y represents at least one element selected from the group consisting of copper, silver, tin, thorium, germanium, nickel, iron, cobalt, titanium, rhenium, chromium, cerium, antimony and magnesium; and a, b, c, d, e and f represent the atomic ratios of molybdenum, vanadium, phosphorus, X, Y and oxygen where, a is 10, b is a number of 6 or less than 6 excluding 0, preferably 0.5 to 3, c is a number of 0.5 to 6, preferably 0.5 to 3, d is a number of 0.5 or less than 0.5 excluding 0, preferably 0.01 to 0.3, e is a number of 5 or less than 5 excluding 0, preferably 0.01 to 1 and f is a number determined by the valence and atomic ratio of the other elements and usually is a number of 35 to 80, and in which a heteropolyacid and an X-metal salt of the heteropolyacid are present in a mixed state both being composed of the element above-mentioned as the constituents and also relates to the catalyst above-mentioned.

The catalyst of the present invention is a catalyst in which a part of the catalyst-structure formed by the coexistence of phosphovanadomolybdic acid and its X-metal salt is occupied by Y-element. The catalyst used in the present invention, as has been described, consists of the coexistence of heteropolyacid composed mainly of phosphovanadomolybdic acid; and its X-metal salt and in the catalyst's X-ray diffraction pattern, the peaks of $2\theta=8.0°$, $8.9°$, $9.3°$, etc. characteristic diffraction peaks of the heteropolyacid and the peaks of $2\theta=26.6°$, $10.8°$, etc. characteristic diffraction peaks of the X-metal salt of the heteropolyacid are observed. However, in the region of the catalyst, in which the amount of coexisting salt is poor, only the peaks due to the acid are observable. As are also shown in the following Examples and Comparative Examples, the catalyst in which the amount of addition of X-component is too much, to the extent in that particularly only the peaks due to X-salt of the heteropolyacid are observed, does not give good results. It is essential to control the amount of addition of X-component within the range of the present invention, and it is one of the remarkable characteristics of the present invention that the addition of X-component is only remarkably effective within the range of the present invention.

Although the catalyst of the present invention is composed of the mixed presence of heteropolyacid and its salt of X-metal, the catalyst may contain oxides and other compounds of the elements composing the catalyst.

In cases where the oxidation of methacrolein is carried out by using the catalyst of the present invention, it is considered that the catalyst is reduced by the reacting gas in the early stage of the reaction to its reduced type.

The catalyst of the present invention is highly active and highly selective and also has a very long life period.

The catalyst of the present invention can be prepared according to the general method of preparation of usual heteropolyacid and X-metal salt of the heteropolyacid, however, it must be avoided that the catalyst obtained turns to ammonium salt of the heteropolyacid.

(A) As a method of the preparation of heteropolyacid, for instance, the following method is applicable in which appropriate compounds of the catalyst-composing elements are at first dispersed in water, etc. and the dispersion is heated and is made to react to dissolve, if necessary with the addition of hydrogen peroxide, and then the reactant is dried to solid. Another method is to bring phosphomolybdic acid or phosphovanadomolybdic acid and compounds of the other catalyst-composing elements into reaction.

(B) As a method of the preparation or an X-salt of the heteropolyacid, for instance, the following method is applicable in which appropriate compounds of the catalyst-composing elements are at first dispersed in a solvent such as water, etc. and the dispersion is heated to react while adding hydrogen peroxide if necessary, and then the solvent is evaporated to leave solid as the catalyst. Another method is to bring phosphovanadomolybdic acid and a compound of X-element (potassium, etc.) into reaction.

Similarly, the catalyst of the present invention is prepared, for instance, by dispersing appropriate compounds of the catalyst-composing elements in a solvent such as water and by heating the dispersion while adding hydrogen peroxide if necessary to bring into reaction, and then by evaporating the solvent to obtain the catalyst as solid. In another way, the heteropolyacid and X-metal salt of the heteropolyacid prepared by the above-mentioned methods (A), (B), etc. are mixed, in a predetermined ratio, in water or an appropriate solvent and then the solvent is evaporated to leave the catalyst as solid. Still another method is to add a compound of X-metal (potassium, etc.) to the solution of heteropolyacid prepared by the methods such as (A) and then evaporate the solvent to obtain the catalyst as solid. As has been described, several methods may be used for the preparation of the catalyst of the present invention, and any method other than above-mentioned may be used provided it gives the catalyst of the present invention as a result. Accordingly, the preparation of the catalyst of the present invention is not limited to the methods above-mentioned.

Most compounds of the elements composing the catalyst may be used as starting materials in preparing the catalyst of the present invention, for instance, molybdenum trioxide, molybdic acid or its salts, and heteromolybdic acid or its salts may be used as the molybdenum compound; orthophosphoric acid, phosphorous acid, hypophosphorous acid or their salts, phosphorus pentoxide, etc. may be used as the phosphorus compound; vanadium pentoxide, vanadyl oxalate, vanadic acid or its salts may be used as the vanadium compound; and nitrates, sulfates, carbonates, phosphates, salts of organic acids, halides, hydrooxides, oxides, etc. may be used as the compounds of X and Y.

Although the catalyst of the present invention shows high catalytic activity without using any carrier, more favorable effects are expected in heat-stability and in life period when it is carried on a usual carrier such as silicon carbide, alpha-alumina, aluminum powder, zeolite, diatomaceous earth, titanium oxide, etc. than when it is used without any carrier.

The mole ratio of molecular oxygen to methacrolein in the catalytic oxidation of methacrolein in vapor phase is preferably of 0.5 to 20 and especially 1 to 10. It is preferable to add water to the reactant feed as a form of vapor at the mole ratio of 1 to 20 to methacrolein. The reactant feed may contain other inert gaseous materials, for instance, nitrogen, carbon dioxide, saturated hydrocarbons, etc. Furthermore, the gaseous reaction product containing methacrolein obtained by the catalytic oxidation of isobutylene or tertiary butanol may be used as the raw material gas as it is.

The reaction temperature in the execution of the present invention is preferably of 200° to 400° C. The feed rate of the gaseous mixture as the raw material is preferably of 100 to 5,000 hr$^{-1}$ (as space velocity=SV) at NTP base, and is more preferably 500 to 3,000 hr$^{-1}$, although in cases where the catalyst of the present invention is used, the increase of SV does not give any large change in the results of reaction and so a reaction with a high SV can be carried out. Furthermore, although the catalytic reaction of the present invention may be carried out under pressure or under reduced pressure, a pressure around the atmospheric one is suitable.

The followings are the more concrete explanation of the present invention by Examples and Comparative Examples, however, the present invention is not limited to such Examples, etc. provided it is not against the point of the present invention.

In addition, in the description of Examples, the value of atomic ratio of oxygen in the composition of catalysts is omitted because it is naturally determined by the atomic valence and atomic ratio of the other elements.

The definitions of the conversion of methacrolein, the yield of methacrylic acid and the selectivity to give methacrylic acid are as follows:

Conversion of methacrolein (%) =

$$\frac{\text{moles of methacrolein reacted}}{\text{moles of methacrolein fed}} \times 100$$

Yield of methacrylic acid (%) =

$$\frac{\text{moles of methacrylic acid produced}}{\text{moles of methacrolein fed}} \times 100$$

Selectivity to methacrylic acid (%) =

$$\frac{\text{Yield of methacrylic acid}}{\text{Conversion of methacrolein}} \times 100$$

EXAMPLE 1

One hundred grams of molybdenum trioxide, 6.3 g of vanadium pentoxide, 1.1 g of copper oxide and 8.0 g of orthophosphoric acid were dispersed in 1,000 ml of de-ionized water and after about 3 hours of heating and stirring of the dispersion, 0.45 g of potassium hydroxide was added to the solution (dispersion changing to solution). The mixture was refluxed for about 3 hours while boiling. The aqueous solution thus formed was evaporated to dryness on a water bath. The composition of the dried product (the catalyst) was $Mo_{10}V_1P_1K_{0.1}Cu_{0.2}$. In the X-ray diffraction pattern of the catalyst, diffraction peaks of $2\theta = 8.0°$, 8.9°, 9.3°, etc. due to heteropolyacid mainly composed of phosphovanadomolybdic acid and faint diffraction peaks of $2\theta = 26.6°$, 10.8°, etc. due to the potassium salt of the heteropolyacid were recognized. The fact shows that in the catalyst obtained a mixture of heteropolyacid mainly composed of phosphovanadomolybdic acid and its potassium salt is present.

This catalyst was crushed to 24–48 mesh, and then packed in a Pyrex-glass tube of 18 mm in inside diameter, which was then immersed in a fluidized bath.

A reactant feed of a composition of methacrolein:oxygen:nitrogen:water vapor = 1:4:16:10 (mole ratio) was passed over the catalyst at an SV of 1,600 hr$^{-1}$ (NTP base) at a reaction temperature of 310° C. The results are shown in Table 1.

EXAMPLES 2–14

The procedure of Example 1 was repeated except that 1.1 g of copper oxide in Example 1 was replaced in each of the examples with 1.6 g of silver oxide; 2.1 g of tin oxide; 3.7 g of thorium oxide; 1.4 g of germanium oxide; 1.0 g of nickel oxide; 1.1 g of iron oxide; 1.1 g of tricobalt tetroxide; 1.1 g of titanium oxide; 3.4 g of rhenium heptoxide; 1.4 g of chromium trioxide; 2.4 g of cerium oxide; 2.0 g of antimony trioxide and 0.6 g of magnesium oxide respectively. The dried products (catalysts) had the compositions shown in Table 1. Oxidation of methacrolein in Examples 2–14 using respective catalyst was carried out under the same conditions as in Example 1 except the reaction temperature (refer to Table 1). Examination of the catalysts in Examples 2–14 by X-ray diffraction pattern showed that a mixture of heteropolyacid mainly composed of phosphovanadomolybdic acid and its X-metal salt was present therein.

EXAMPLE 18

The procedure of Example 1 was repeated except that 0.45 g of potassium hydroxide was replaced with both 0.23 g of potassium hydroxide and 0.5 g of cesium hydroxide to prepare a catalyst, and oxidation of methacrolein was carried out using the catalyst thus obtained under the same conditions as in Example 1. The composition of the catalyst and the results of oxidation are shown in Table 1.

COMPARATIVE EXAMPLE 1

A catalyst was prepared in the same manner as in Example 1, however, without adding 0.45 g of potassium hydroxide and the total continued refluxing time under boiling of 6 hours. The dried product (catalyst) had a composition of $Mo_{10}V_1P_1Cu_{0.2}$. Oxidation of methacrolein was carried out under the same conditions as in Example 1 except the reaction temperature of 320° C. The results were: conversion of methacrolein of 96.3%; yield of methacrylic acid of 71.1%; and selectivity to methacrylic acid of 73.8%.

COMPARATIVE EXAMPLE 2

A catalyst was prepared in the same manner as in Example 1, however, instead of 0.45 g of potassium hydroxide, 9 g of potassium hydroxide was used to obtain a catalyst of the composition of $Mo_{10}V_1P_1K_2Cu_{0.2}$. Oxidation of methacrolein was carried out using the catalyst thus obtained under the same conditions as in Example 1 with the following results: conversion of

TABLE 1

| Example | Composition of catalyst | Reaction temperature (°C.) | Conversion of methacrolein (%) | Yield of methacrylic acid (%) | Selectivity to methacrylic acid (%) |
| --- | --- | --- | --- | --- | --- |
| 1 | $Mo_{10}V_1P_1K_{0.1}Cu_{0.2}$ | 310 | 95.1 | 74.8 | 78.7 |
| 2 | $Mo_{10}V_1P_1K_{0.1}Ag_{0.2}$ | 330 | 92.5 | 70.0 | 75.7 |
| 3 | $Mo_{10}V_1P_1K_{0.1}Sn_{0.2}$ | 325 | 91.3 | 69.1 | 75.7 |
| 4 | $Mo_{10}V_1P_1K_{0.1}Th_{0.2}$ | 315 | 95.5 | 73.2 | 76.6 |
| 5 | $Mo_{10}V_1P_1K_{0.1}Ge_{0.2}$ | 325 | 94.0 | 72.6 | 77.2 |
| 6 | $Mo_{10}V_1P_1K_{0.1}Ni_{0.2}$ | 330 | 92.3 | 70.1 | 75.9 |
| 7 | $Mo_{10}V_1P_1K_{0.1}Fe_{0.2}$ | 310 | 94.1 | 73.6 | 78.2 |
| 8 | $Mo_{10}V_1P_1K_{0.1}Co_{0.2}$ | 325 | 90.0 | 70.6 | 78.4 |
| 9 | $Mo_{10}V_1P_1K_{0.1}Ti_{0.2}$ | 325 | 94.6 | 71.3 | 75.4 |
| 10 | $Mo_{10}V_1P_1K_{0.1}Re_{0.2}$ | 310 | 96.5 | 73.8 | 76.5 |
| 11 | $Mo_{10}V_1P_1K_{0.1}Cr_{0.2}$ | 330 | 93.5 | 70.5 | 75.4 |
| 12 | $Mo_{10}V_1P_1K_{0.1}Ce_{0.2}$ | 315 | 94.6 | 73.4 | 77.6 |
| 13 | $Mo_{10}V_1P_1K_{0.1}Sb_{0.2}$ | 325 | 92.0 | 69.5 | 75.5 |
| 14 | $Mo_{10}V_1P_1K_{0.1}Mg_{0.2}$ | 330 | 91.0 | 68.9 | 75.7 |
| 15 | $Mo_{10}V_1P_1Cs_{0.1}Cu_{0.2}$ | 310 | 94.3 | 74.1 | 78.6 |
| 16 | $Mo_{10}V_1P_1Rb_{0.1}Cu_{0.2}$ | 310 | 91.9 | 72.3 | 78.7 |
| 17 | $Mo_{10}V_1P_1Tl_{0.1}Cu_{0.2}$ | 310 | 92.3 | 72.7 | 78.8 |
| 18 | $Mo_{10}V_1P_1K_{0.05}Cs_{0.05}Cu_{0.2}$ | 310 | 95.3 | 75.0 | 78.7 |

EXAMPLES 15–17

The procedure of Example 1 was repeated except that 0.45 g of potassium hydroxide was replaced with the following respective compounds: 1.0 g of cesium hydroxide; 0.7 g of rubidium hydroxide; and 1.6 g of thallium hydroxide. The dried products (catalysts) had composition shown in Table 1. Oxidation of methacrolein was carried out using each one of these catalysts under the same conditions as in Example 1. The results are shown in Table 1. Examination of the catalysts in Examples 15–17 by X-ray diffraction measurement showed that a mixture of heteropolyacid mainly composed of phosphovanadomolybdic acid and its X-metal salt was present therein.

methacrolein of 49.6%; yield of methacrylic acid of 40.8% and selectivity to methacrylic acid of 82.3%. Examination of the catalyst by X-ray diffraction showed that the potassium salt of heteropolyacid predominated in the catalyst. Further, after carrying out a continuous run of the oxidation for 30 days, conversion of methacrolein, yield of methacrylic acid, and selectivity to methacrylic acid were respectively 35.1; 28.0 and 79.8%.

EXAMPLES 19–24

Following the procedure of Example 1, dried products (catalysts) having respective compositions shown in Table 2 were obtained and oxidation of methacrolein was carried out by using the respective catalyst. The results are also shown in Table 2.

TABLE 2

| Example | Composition of catalyst | Reaction temperature (°C.) | Conversion of methacrolein (%) | Yield of methacrylic acid (%) | Selectivity to methacrylic acid (%) |
|---|---|---|---|---|---|
| 19 | $Mo_{10}V_1P_1K_{0.5}Cu_{0.2}$ | 320 | 87.3 | 71.8 | 82.2 |
| 20 | $Mo_{10}V_1P_1K_{0.2}Cu_{0.2}$ | 315 | 95.9 | 74.5 | 78.0 |
| 21 | $Mo_{10}V_1P_1K_{0.1}Cu_{0.5}$ | 300 | 95.8 | 73.8 | 77.0 |
| 22 | $Mo_{10}V_1P_1K_{0.1}Cu_{1.0}$ | 285 | 94.3 | 70.9 | 75.2 |
| 23 | $Mo_{10}V_2P_1K_{0.1}Cu_{0.2}$ | 320 | 90.2 | 70.2 | 77.8 |
| 24 | $Mo_{10}V_1P_2K_{0.1}Cu_{0.2}$ | 325 | 94.8 | 74.3 | 78.4 |

EXAMPLES 25–29

In the procedure of Example 1, in addition to 100 g of molybdenum trioxide, 6.3 g of vanadium pentoxide, 1.1 g of copper oxide and 8.0 g of orthophosphoric acid, the following compounds were respectively dispersed in the de-ionized water: 1.0 g of tin oxide; 1.8 g of thorium oxide; 0.7 g of germanium oxide; 0.6 g of iron oxide or rhenium heptoxide. The procedures after making the dispersion were the same as in Example 1 in preparing catalysts. Their composition and the results of oxidation of methacrolein using each one catalyst under the same conditions as in Example 1 are shown in Table 3. Examination of the catalysts by X-ray diffraction showed that a mixture of heteropolyacid mainly composed of phosphovanadomolybdic acid and its salt was present in the catalysts.

EXAMPLE 30

A catalyst was prepared by the procedure of Example 1, however, 1.1 g of iron oxide plus 1.2 g of cerium oxide were used instead of 1.1 g of copper oxide to obtain the catalyst with a composition shown in Table 3. Oxidation of methacrolein was carried out by using the catalyst thus obtained under the same conditions as in Example 1, results of oxidation using the catalyst are also shown in Table 3. The presence of a mixture of heteropolyacid mainly composed of phosphovanadomolybdic acid and its salt was confirmed by its X-ray diffraction analysis.

EXAMPLE 31

A catalyst was prepared by the procedure of Example 1, however, 1.1 g of iron oxide and 1.0 g of tin oxide were also dispersed in the de-ionized water together with the compounds used in Example 1. The composition of the dried product (catalyst) and the results of oxidation of methacrolein under the same conditions as in Example 1 using the catalyst are shown in Table 3.

EXAMPLE 32

A catalyst was prepared by the procedure of Example 1, however, 1.1 g of iron oxide and 0.7 g of germanium oxide were also dispersed in the de-ionized water together with the compounds used in Example 1. The composition of the catalyst thus obtained and the results of oxidation of methacrolein using the catalyst under the same conditions as in Example 1 are shown in Table 3.

TABLE 3

| Example | Composition of catalyst | Reaction temperature (°C) | Conversion of methacrolein (%) | Yield of methacrylic acid (%) | Selectivity to methacrylic acid (%) |
|---|---|---|---|---|---|
| 25 | $Mo_{10}V_1P_1K_{0.1}Cu_{0.2}Sn_{0.1}$ | 310 | 95.8 | 74.8 | 78.1 |
| 26 | $Mo_{10}V_1P_1K_{0.1}Cu_{0.2}Th_{0.1}$ | 310 | 94.6 | 74.5 | 78.8 |
| 27 | $Mo_{10}V_1P_1K_{0.1}Cu_{0.2}Ge_{0.1}$ | 310 | 96.1 | 75.5 | 78.6 |
| 28 | $Mo_{10}V_1P_1K_{0.1}Cu_{0.2}Fe_{0.1}$ | 305 | 96.0 | 75.6 | 78.8 |
| 29 | $Mo_{10}V_1P_1K_{0.1}Cu_{0.2}Re_{0.1}$ | 305 | 95.8 | 74.9 | 78.2 |
| 30 | $Mo_{10}V_1P_1K_{0.1}Fe_{0.2}Ce_{0.1}$ | 305 | 94.5 | 73.8 | 78.1 |
| 31 | $Mo_{10}V_1P_1K_{0.1}Cu_{0.2}Fe_{0.1}Sn_{0.1}$ | 305 | 96.3 | 76.4 | 79.3 |
| 32 | $Mo_{10}V_1P_1K_{0.1}Cu_{0.2}Fe_{0.1}Ge_{0.1}$ | 305 | 95.2 | 75.8 | 79.6 |

EXAMPLE 33

Each reaction of oxidation in Examples 1–32 was carried out continuously for 30 days. Substantial change of the results of each reaction was not found. The results of the reaction after 30 day's continued operation are shown in Table 4.

TABLE 4

| Example of continuous operation for 30 days | Conversion of methacrolein (%) | Yield of methacrylic acid (%) | Selectivity to methacrylic acid (%) |
|---|---|---|---|
| 1 | 95.5 | 75.0 | 78.5 |
| 2 | 92.7 | 70.3 | 75.8 |
| 3 | 92.0 | 69.6 | 75.7 |
| 4 | 95.6 | 73.5 | 76.1 |
| 5 | 94.5 | 73.0 | 77.2 |
| 6 | 92.7 | 70.3 | 75.8 |
| 7 | 94.3 | 73.8 | 78.3 |
| 8 | 90.2 | 70.7 | 78.4 |
| 9 | 94.6 | 71.2 | 75.3 |
| 10 | 96.8 | 73.5 | 75.9 |
| 11 | 93.8 | 70.8 | 75.5 |
| 12 | 94.8 | 73.7 | 77.7 |
| 13 | 92.3 | 69.6 | 75.4 |
| 14 | 91.8 | 69.3 | 75.5 |
| 15 | 94.9 | 74.5 | 78.5 |
| 16 | 92.8 | 73.0 | 78.7 |
| 17 | 93.5 | 73.3 | 78.4 |
| 18 | 95.8 | 75.2 | 78.5 |
| 19 | 87.5 | 71.9 | 82.2 |
| 20 | 95.9 | 74.8 | 78.0 |
| 21 | 95.9 | 74.0 | 77.2 |
| 22 | 94.2 | 70.8 | 75.2 |

TABLE 4-continued

| Example of continuous operation for 30 days | Conversion of methacrolein (%) | Yield of methacrylic acid (%) | Selectivity to methacrylic acid (%) |
| --- | --- | --- | --- |
| 23 | 90.8 | 70.4 | 77.5 |
| 24 | 95.1 | 74.5 | 78.3 |
| 25 | 96.2 | 75.0 | 78.0 |
| 26 | 94.9 | 74.5 | 78.5 |
| 27 | 96.6 | 75.8 | 78.5 |
| 28 | 96.2 | 75.7 | 78.7 |
| 29 | 96.1 | 75.0 | 78.0 |
| 30 | 94.7 | 73.9 | 78.0 |
| 31 | 96.5 | 76.5 | 79.3 |
| 32 | 95.5 | 75.9 | 79.5 |

What is claimed is:

1. A process for producing methacrylic acid by oxidation of methacrolein in vapor phase with molecular oxygen or a gas containing molecular oxygen characterized in that said oxidation of methacrolein is carried out in the presence of a catalyst of a mixture of a heteropolyacid and its salt which has a composition represented by the following formula:

$$Mo_aV_bP_cX_dY_eO_f$$

wherein Mo, V, P and O respectively represent molybdenum, vanadium, phosphorus and oxygen; X represents at least one element selected from the group consisting of potassium, rubidium, cesium and thallium; Y represents at least one element selected from the group consisting of copper, silver, tin, thorium, germanium, nickel, iron cobalt, titanium, rhenium, cerium and antimony and a, b, c, d, e and f represent the atomic ratio of said elements where a is 10, b is a number of 6 or less than 6 excluding 0, c is a number of 0.5 to 6, d is a number of 0.5 or less than 0.5 excluding 0, e is a number of 5 or less than 5 excluding 0 and f is a number determined by the valence and atomic ratio of the other elements.

2. The process according to claim 1, wherein a is 10, b is 0.5 to 3, c is 0.5 to 3, d is 0.01 to 0.3 and e is 0.01 to 1.

3. The process according to claim 1, wherein Y is copper.

4. The process according to claim 1, wherein the reaction temperature of said oxidation is between 200° and 400° C.

5. The process according to claim 1, wherein said oxidation is conducted in the presence of water vapor.

* * * * *